United States Patent
Akiyama et al.

(10) Patent No.: US 11,808,764 B2
(45) Date of Patent: Nov. 7, 2023

(54) MEMBRANE CARRIER FOR LIQUID SAMPLE TEST KIT, LIQUID SAMPLE TEST KIT, METHOD OF MANUFACTURING LIQUID SAMPLE TEST KIT, TEST METHOD OF LIQUID SAMPLE, AND MEMBRANE CARRIER

(71) Applicant: DENKA COMPANY LIMITED, Tokyo (JP)

(72) Inventors: Yuto Akiyama, Tokyo (JP); Kenji Monden, Tokyo (JP)

(73) Assignee: DENKA COMPANY LIMITED, Tokyo (JP)

( * ) Notice: Subject to any disclaimer, the term of this patent is extended or adjusted under 35 U.S.C. 154(b) by 128 days.

(21) Appl. No.: 16/770,517

(22) PCT Filed: Dec. 10, 2018

(86) PCT No.: PCT/JP2018/045367
§ 371 (c)(1),
(2) Date: Jun. 5, 2020

(87) PCT Pub. No.: WO2019/117102
PCT Pub. Date: Jun. 20, 2019

(65) Prior Publication Data
US 2021/0181194 A1    Jun. 17, 2021

(30) Foreign Application Priority Data
Dec. 11, 2017 (JP) .................... 2017-236604

(51) Int. Cl.
*G01N 33/543* (2006.01)
(52) U.S. Cl.
CPC .. *G01N 33/54386* (2013.01); *G01N 33/54393* (2013.01)

(58) Field of Classification Search
None
See application file for complete search history.

(56) References Cited

U.S. PATENT DOCUMENTS

| 7,413,880 | B2 | 8/2008 | Aki et al. ............... 435/100 |
| 10,613,086 | B2 | 4/2020 | Kato et al. | |
| 2006/0051237 | A1* | 3/2006 | Wang ............ G01N 33/5302 422/417 |
| 2006/0154301 | A1 | 7/2006 | Aki et al. ............... 435/7.1 |

(Continued)

FOREIGN PATENT DOCUMENTS

| CN | 1658972 A | 8/2005 |
| CN | 1818652 A | 8/2006 |

(Continued)

OTHER PUBLICATIONS

International Search Report dated Mar. 15, 2019, issued by the Japanese Patent Office in corresponding application PCT/JP2018/045367.

(Continued)

*Primary Examiner* — Ann Montgomery
*Assistant Examiner* — Jennifer H. Tieu
(74) *Attorney, Agent, or Firm* — Stein IP, LLC

(57) ABSTRACT

Provided is a membrane carrier for a liquid sample test kit (3) that detects a substance to be detected in a liquid sample, the liquid sample test kit including at least one flow path (2) capable of transporting the liquid sample, in which a microstructure that causes a capillary action for transporting the liquid sample is provided on a bottom surface of the flow path (2), and a level difference at which a height level of the bottom surface changes, is provided in the flow path (2). The membrane carrier preferably has a detection zone for detecting a substance to be detected in the liquid sample.

17 Claims, 9 Drawing Sheets

(56) References Cited

U.S. PATENT DOCUMENTS

| | | | |
|---|---|---|---|
| 2007/0266777 A1* | 11/2007 | Bergman | B01L 3/502753 73/61.41 |
| 2007/0269906 A1* | 11/2007 | Wang | G01N 33/536 422/68.1 |
| 2009/0016932 A1 | 1/2009 | Curcio et al. | 422/68.1 |
| 2009/0155927 A1 | 6/2009 | Higashino et al. | 436/180 |
| 2010/0041154 A1* | 2/2010 | Ohman | G01N 33/543 422/68.1 |
| 2011/0284110 A1* | 11/2011 | Gagnon | B01L 3/502707 |
| 2013/0084580 A1 | 4/2013 | Wada et al. | 435/7.1 |
| 2014/0093868 A1 | 4/2014 | Wada et al. | 435/5 |
| 2014/0140891 A1* | 5/2014 | Fiering | B01L 3/502753 422/68.1 |
| 2016/0038936 A1* | 2/2016 | Ding | B01L 3/5023 435/287.7 |
| 2016/0153878 A1* | 6/2016 | Candon | G01N 33/558 422/520 |
| 2016/0370368 A1 | 12/2016 | Kato et al. | |
| 2018/0266954 A1* | 9/2018 | Nagae | G01N 21/64 |

FOREIGN PATENT DOCUMENTS

| | | | |
|---|---|---|---|
| CN | 103033610 A | 4/2013 | |
| CN | 105452863 A | 3/2016 | |
| JP | 2007-530938 A | 11/2007 | |
| JP | 2009-258136 A | 11/2009 | |
| JP | 4597664 B2 | 12/2010 | |
| JP | 2012-524894 A | 10/2012 | |
| JP | 2013-113633 A | 6/2013 | |
| JP | 2014-62820 A | 4/2014 | |
| JP | 2014-210925 A | 5/2014 | |
| JP | 5609648 B2 | 9/2014 | |
| JP | 5821430 B2 | 10/2015 | |
| JP | 2016-11943 A | 1/2016 | |
| JP | 2017-78664 A | 4/2017 | |
| WO | WO 2015/098784 A1 | 7/2015 | |
| WO | WO 2016/051974 A1 | 4/2016 | |
| WO | WO 2016/098740 A1 | 6/2016 | |
| WO | WO-2016098740 A1 * | 6/2016 | G01N 35/02 |

OTHER PUBLICATIONS

Chinese Office Action dated Feb. 14, 2023, issued by the China National Intellectual Property Administration in corresponding application CN 201880079450.0.

Chinese Office Action in the corresponding Chinese patent application (No. 2018813979450.0), dated Aug. 15, 2023.

* cited by examiner

MEMBRANE CARRIER FOR LIQUID SAMPLE TEST KIT, LIQUID SAMPLE TEST KIT, METHOD OF MANUFACTURING LIQUID SAMPLE TEST KIT, TEST METHOD OF LIQUID SAMPLE, AND MEMBRANE CARRIER

CROSS-REFERENCE TO RELATED APPLICATIONS

This application is a national stage of International Application No. PCT/JP2018/045367, filed Dec. 10, 2018, which claims the benefit of Japanese Application No. 2017-236604, filed Dec. 11, 2017, in the Japanese Patent Office, the disclosures of which are incorporated herein by reference.

TECHNICAL FIELD

The present invention relates to a membrane carrier for a liquid sample test kit, a liquid sample test kit, a method of manufacturing a liquid sample test kit, a test method of a liquid sample, and a membrane carrier.

BACKGROUND ART

In recent years, a Point of Care Test (POCT) reagent, which measures an affliction of an infectious disease, pregnancy, a blood glucose level, and the like by using an antigen-antibody reaction and the like, has attracted attention. The POCT reagent has characteristics that a result can be determined in a short time, a use method is simple, and the cost is low. With these characteristics, the POCT reagent is frequently used for medical examinations and periodic medical examinations at a stage where the symptoms are mild, and is an important medical examination tool in home medical care, which is expected to increase in the future.

In many POCT reagents, a determination is made by introducing a liquid sample such as blood into a test kit and detecting a specific substance to be detected contained therein. As a method for detecting a specific substance to be detected from the liquid sample, an immunochromatography method is often used. An immunochromatography method refers to a technique in which a substance to be detected and a label are bound while a liquid dropped on a membrane carrier of a test kit moves on the membrane carrier, these specifically bind to a substance (hereinafter, referred to as detection substance) immobilized in the test kit, and a change in color or mass generated as a result is detected. The detection substance may be referred to as a reagent.

As a technique of detecting a substance to be detected, a method of detecting a change in color caused by using colored latex particles, fluorescent latex particles, metal colloidal particles, and the like as a label via an optical measurement device such as an absorbance measurement device is well known.

As a POCT reagent for optically determining the change in color, a lateral flow type kit using a nitrocellulose membrane is often used (Patent Document 1). The nitrocellulose membrane has a large number of fine holes having a diameter of about several μm, and the liquid sample moves in the holes by capillary force.

However, since the nitrocellulose membrane is derived from a natural product and a pore diameter and a way of connecting the pores are not uniform, there occurs a difference in a flow rate of the liquid sample flowing in each membrane. Patent Document 2 discloses a technique of controlling the flow rate. However, Patent Document 2 has a flow path which is porous body. The present invention has a flow path having a microstructure having a convex portion, and is different from Patent Document 2. Patent Document 2 uses a nitrocellulose membrane, and thus had a problem that the pore diameter and the way of connecting the pores are not uniform. In a case where a difference occurs in the flow rates, the time required to detect a substance to be detected is also changed, and as a result, the substance to be detected may be erroneously determined as non-detection before binding occurs.

In order to solve the above-mentioned problem, a technique of artificially preparing a fine flow path has been devised (Patent Documents 3 to 7). By using this technique, it is possible to prepare a membrane carrier having a uniform structure. Therefore, it is possible to decrease a possibility of erroneously determining a substance to be detected as non-detection before binding occurs.

In the above patent documents, the flow path structure in the system is uniform, and thus there is no limit in detection performance. Patent Document 8 discloses a technique for improving the detection performance at a time of using an artificial fine flow path, in which a groove-shaped flow path for the purpose of flow rate control is combined with a pillar-shaped flow path for the purpose of improving sensitivity.

RELATED DOCUMENT

Patent Document

[Patent Document 1] Japanese Unexamined Patent Publication No. 2014-062820
[Patent Document 2] International Publication No. WO 2016/051974
[Patent Document 3] Japanese Patent No. 4597664
[Patent Document 4] PCT Japanese Translation Patent Publication No. 2012-524894
[Patent Document 5] Japanese Patent No. 5609648
[Patent Document 6] Japanese Unexamined Patent Publication No. 2016-011943
[Patent Document 7] Japanese Unexamined Patent Publication No. 2013-113633
[Patent Document 8] Japanese Patent No. 5821430
[Patent Document 9] International Publication No. WO 2016/098740

SUMMARY OF THE INVENTION

Technical Problem

However, in the techniques disclosed in Patent Documents 1 to 8, attention is focused only on the detection substance and not on the flow of the substance to be detected or the flow of the label. In a system using an artificial fine flow path, the flow easily becomes a simple laminar flow. As a result, it becomes difficult to sufficiently stir the substance to be detected and the label, and this becomes a factor of deteriorating the detection performance. In particular, in a lateral flow type immunochromatography method, the detection system is simple, and the influence of the flow path structure is likely to be reflected in the test result.

Patent Document 9 discloses a membrane carrier for a liquid sample test kit that detects a substance to be detected in a liquid sample, in which at least one flow path capable of transporting the liquid sample is provided, and the microstructure that generates a capillary action for transporting the liquid sample is provided on a bottom surface of the flow path. However, Patent Document 9 does not disclose a level difference.

In view of the above problems, an object of the present invention is to provide a test kit capable of highly sensitive determination in an immunochromatography method capable of confirming that a substance to be detected has been detected by an optical technique, for example.

That is, the present invention is as follows.

(1) A membrane carrier for a liquid sample test kit that detects a substance to be detected in a liquid sample, the membrane carrier including:

at least one integrally-molded flow path capable of transporting the liquid sample, in which a microstructure that causes a capillary action for transporting the liquid sample is provided on a bottom surface of the flow path, in which at least one level difference, at which a height level of the bottom surface changes, is provided in the flow path, and in which the level difference is provided such that the height level of the bottom surface on a downstream side is higher than that on an upstream side in the transporting direction of the liquid sample.

(2) The membrane carrier for a liquid sample test kit according to (1), in which the microstructure has any one of a cone, a pyramid, a truncated cone, a truncated pyramid, a cylinder, a polygonal prism, a hemisphere, and a semi-ellipsoid.

(3) The membrane carrier for a liquid sample test kit according to (1) or (2), in which an amount of change in the height level of the bottom surface at the level difference is equal to or less than twice the height of the microstructure on the upstream side of the level difference.

(4) The membrane carrier for a liquid sample test kit according to any one of (1) to (3), in which an inclination is provided on the downstream side of the level difference in the flow path such that the height level of the bottom surface approaches the height level on the upstream side of the level difference.

(5) The membrane carrier for a liquid sample test kit according to any one of (1) to (4), in which the microstructure changes between the upstream side and the downstream side of the level difference with the level difference as a boundary.

(6) The membrane carrier fora liquid sample test kit according to any one of (1) to (5), in which the height of the microstructure on the downstream side is smaller than that on the upstream side with the level difference as a boundary.

(7) The membrane carrier fora liquid sample test kit according to any one of (1) to (6), in which a height of the microstructure is equal to or more than 10 μm and equal to or less than 500 μm in the flow path.

(8) A liquid sample test kit that detects a substance to be detected in a liquid sample, the liquid sample test kit including:

the membrane carrier for a liquid sample test kit according to any one of (1) to (7), in which the membrane carrier includes a detection zone that detects the substance to be detected in the liquid sample, and in which in the detection zone, a change in color occurs at a time when the substance to be detected is detected.

(9) The liquid sample test kit according to (8), in which the detection zone is provided on an inclined portion in the flow path.

(10) The liquid sample test kit according to (8) or (9), in which a label having an antibody specifically reacting with the substance to be detected in the liquid sample or an antigen-binding fragment thereof is provided in at least a part of the liquid sample test kit so as to react with the substance to be detected, and in which the change in color occurs due to the label that binds to the substance to be detected.

(11) The liquid sample test kit according to (10), in which the label is a particle in which the antibody or the antigen-binding fragment is bound to a colored latex particle or a fluorescent latex particle.

(12) The liquid sample test kit according to (10) or (11), in which a detection substance that detects the substance to be detected is immobilized in the detection zone, and the change in color occurs by the label being held in the detection zone by the detection substance and being colored.

(13) A method of manufacturing the liquid sample test kit according to any one of (8) to (12), the method including: immobilizing a detection substance in the detection zone that causes the change in color by holding the substance to be detected in the detection zone.

(14) A test method of a liquid sample using the liquid sample test kit according to any one of (8) to (12), the test method including: mixing the liquid sample with a label specifically binding to the substance to be detected in the liquid sample to prepare a mixture liquid sample, and binding the substance to be detected and the label to each other; dropping the mixture liquid sample in a dropping zone provided on the membrane carrier; transporting the mixture liquid sample from the dropping zone to the detection zone by the microstructure; and detecting a change in color in the detection zone.

(15) A membrane carrier for detecting a substance to be detected in a liquid sample, including: at least one flow path, in which a microstructure is provided on a bottom surface of the flow path, in which at least one level difference is provided in the flow path, and in which the level difference is provided such that a height level of the bottom surface on a downstream side is higher than that on an upstream side in a transporting direction of the liquid sample.

According to the present invention, in an immunochromatography method capable of confirming that a substance to be detected has been detected by an optical technique, it is possible to provide a test kit capable of highly sensitive determination.

BRIEF DESCRIPTION OF THE DRAWINGS

The object, other objects, characteristics, and advantages will be further apparent from preferable embodiments to be described later and the following drawings accompanying thereof.

DESCRIPTION OF EMBODIMENTS

Figure 1:
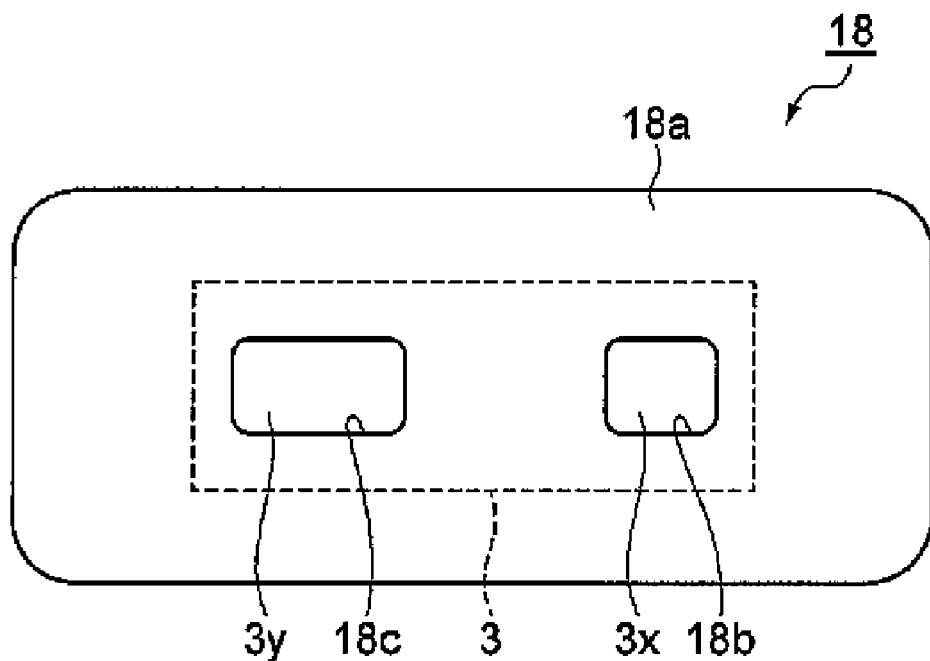
FIG. 1 is an example of an embodiment according to the present invention, and is a schematic top view of a test kit.

Hereinafter, embodiments of the present invention will be described with reference to the drawings. In all the drawings, like components are denoted by common reference numerals, and description thereof will not be repeated. In addition, the drawing is a schematic view, and does not match the actual dimensional ratio.

The membrane carrier for a liquid sample test kit of the present embodiment refers to a membrane carrier for a liquid sample test kit that detects a substance to be detected in a liquid sample, for example.

Here, the substance to be detected is not limited at all, and may be any substance that can have an antigen-antibody reaction with an antibody, such as various pathogens and various clinical labels. Specific examples of the substance to be detected include virus antigens such as influenza virus, norovirus, adenovirus, RS virus, HAV, HBs, and HIV, bacterial antigens such as MRSA, group A *streptococcus*, group B *streptococcus*, and genus *Legionella* bacteria, toxins produced by viruses, hormones such as *mycoplasma, Chlamydia trachomatis*, and human chorionic gonadotropin, C-reactive protein, myoglobin, cardiac troponin, various tumor labels, pesticides, and environmental hormones, but are not limited thereto. In particular, in a case where the substance to be detected is a substance that is urgently required in detection and therapeutic measures such as influenza virus, norovirus, C-reactive protein, myoglobin, and cardiac troponin, the liquid sample test kit and the membrane carrier according to the present embodiment are greatly useful. The substance to be detected may be an antigen capable of inducing an immune reaction alone, or may not be capable of inducing an immune reaction alone. However, the substance to be detected may be a hapten capable of inducing an immune reaction in a case being bound by an antigen-antibody reaction with an antibody. The substance to be detected is usually in a state of being floated or dissolved in the liquid sample. The liquid sample may be a sample in which the substance to be detected is floated or dissolved in a buffer solution, for example.

The liquid sample test kit (hereinafter, also referred to as test kit) according to the present embodiment detects a substance to be detected in a liquid sample. FIG. 1 is a schematic top view of the test kit. For example, as illustrated in FIG. 1, the test kit 18 includes a membrane carrier 3 and a housing 18a that houses the membrane carrier 3. The membrane carrier 3 has, on a surface thereof, a dropping zone 3x where a liquid sample is dropped, and a detection zone 3y for detecting the substance to be detected in the liquid sample. The dropping zone 3x is exposed at a first opening 18b of the housing 18a. The detection zone 3y is exposed at a second opening 18c of the housing 18a.

Figure 2:
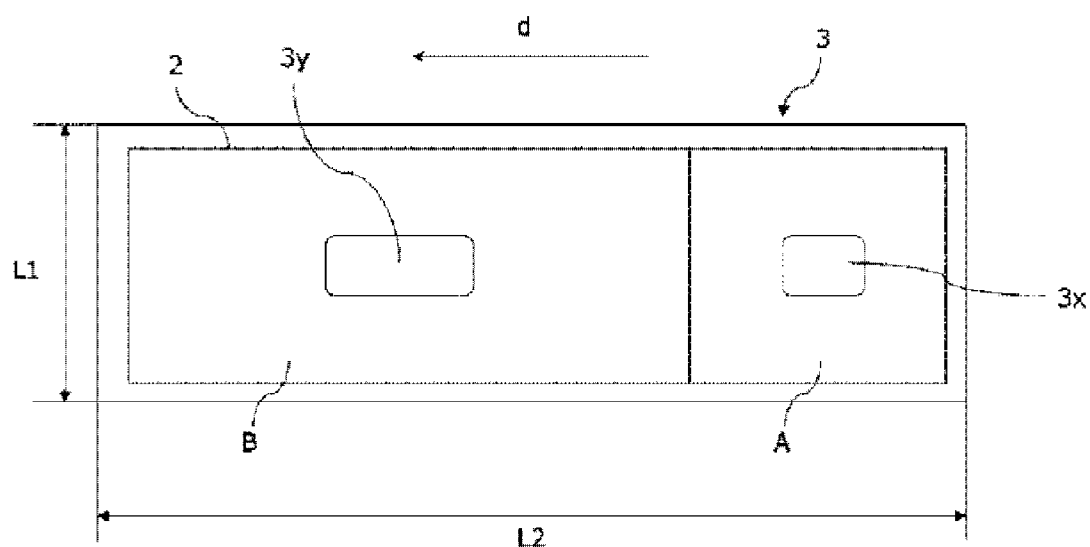
FIG. 2 is an example of an embodiment according to the present invention, and is a schematic top view of a membrane carrier.

FIG. 2 is a schematic top view of the membrane carrier 3. As illustrated in FIG. 2, the membrane carrier 3 includes at least one flow path 2 that transports a liquid sample. The flow path 2 is preferably provided by integral molding. A microstructure is provided on the bottom surface of the flow path 2 (not illustrated, details will be described later). The microstructure is positioned at least between the dropping zone 3x and the detection zone 3y. The microstructure may be provided over the entire surface of the membrane carrier 3. The entire surface of the membrane carrier 3 may be the flow path 2 of the liquid sample. The microstructure causes capillary action. Due to the capillary action of the microstructure, the liquid sample is transported to the detection zone 3y (along a transporting direction d) from the dropping zone 3x via the microstructure. In a case where the substance to be detected in the liquid sample is detected in the detection zone 3y, color of the detection zone 3y changes.

The entire shape of the membrane carrier 3 is not particularly limited, but may be, for example, a polygon such as a square, a circle, or an ellipse. In a case where the membrane carrier 3 is a square, a vertical width (length in a short-side direction) L1 of the membrane carrier 3 may be equal to or more than 2 mm and equal to or less than 100 mm, for example, and a horizontal width (length in a long-side direction) L2 of the membrane carrier 3 may be equal to or more than 2 mm and equal to or less than 100 mm, for example. A thickness of the membrane carrier excluding a height of the microstructure may be equal to or more than 0.1 mm and equal to or less than 10 mm, for example.

The microstructure is preferably formed of any one of a cone, a pyramid, a truncated cone, a truncated pyramid, a cylinder, a polygonal prism, a hemisphere, and a semi-ellipsoid. FIGS. 3(a) to 6(b) each illustrate an example of a microstructure provided on the bottom surface of the flow path and a convex portion constituting the microstructure in the present embodiment. In FIGS. 3(a) to 6(b), FIGS. 3(a), 4(a), 5(a), and 6(a) each are a bird's-eye view (top view) of the microstructure, and FIGS. 3(b), 4(b), 5(b), and 6(b) each are a perspective view of a convex portion constituting the microstructure illustrated in FIGS. 3(a), 4(a), 5(a), and 6(a). As illustrated in FIGS. 3(a) to 6(b), a microstructure 7 is an entire body (aggregate) of a convex portion 8. That is, the microstructure 7 includes a flat portion 9 corresponding to the bottom surface of the flow path 2 of the liquid sample, and a plurality of convex portions 8 protruding from the flat portion 9. Due to the capillary action, a space between the plurality of convex portions 8 functions as the flow path 2 for transporting the liquid sample along a surface of the membrane carrier 3. In other words, a void in the microstructure 7 functions as the flow path 2 for transporting the liquid sample along the surface of the membrane carrier 3 by the capillary action. The plurality of convex portions 8 may be regularly or translationally arranged in line on the surface of the membrane carrier 3.

For example, as illustrated in FIG. 3, the shape of the convex portion 8a may be a cone. For example, as illustrated in FIG. 4, the shape of the convex portion 8b may be a quadrangular pyramid. For example, as illustrated in FIG. 5, the shape of the convex portion 8c may be a hexagonal pyramid. For example, as illustrated in FIG. 6, the shape of the convex portion 8d may be a horizontally disposed triangular prism (a triangular prism arranged such that one side surface (a square surface) of the triangular prism is in contact with the flat portion 9). From a viewpoint that the entire surface of the membrane carrier 3 can be visually recognized at a time when the microstructure 7 is viewed from a bird's-eye view (viewed from above), and a change in color at a time when the substance to be detected has been detected is easily confirmed by an optical technique, among these, a conical structure such as a cone or a pyramid is suitable as the shape of the convex portion 8. In the conical structure, a cone is suitable as the shape of the convex portion 8.

The shape of the convex portion 8 constituting the microstructure 7 does not need to be a geometrically accurate shape, and may be a shape with rounded corners or a shape with fine irregularities on the surface.

Figure 8:
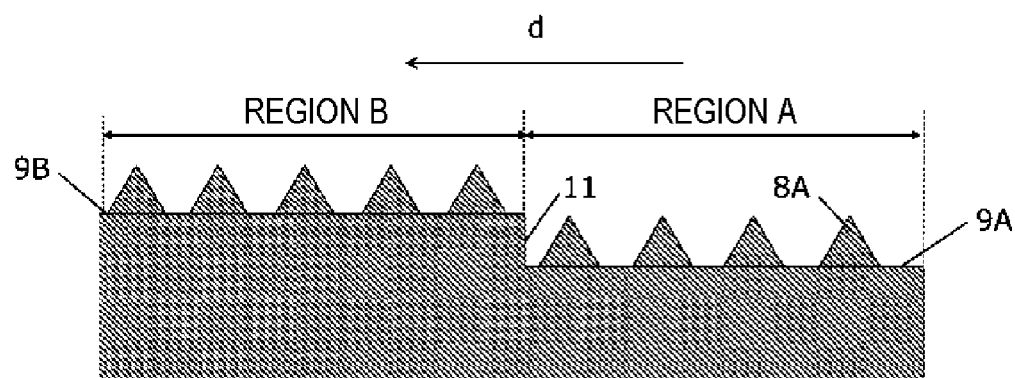
FIG. 8 is an example of an embodiment according to the present invention, and is a sectional view of a level difference provided in a flow path.
Figure 9:
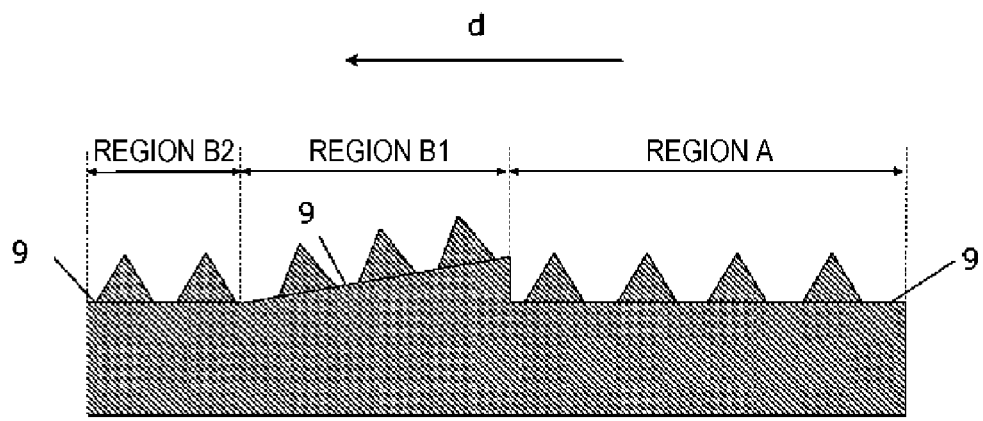
FIG. 9 is an example of an embodiment according to the present invention, and is a sectional view of a level difference provided in a flow path.

The membrane carrier 3 is provided with a level difference 11 in which the height level of the bottom surface of the flow path 2 changes. FIG. 8 illustrates a level difference viewed from a direction perpendicular to a direction of a thickness of the membrane carrier and a transporting direction of the liquid sample. As illustrated in FIG. 9, a region B downstream of the level difference may be inclined such that the height level of the bottom surface approaches a region A upstream of the level difference.

The level difference 11 is preferably one in which the height level of the bottom surface of the flow path 2 changes discontinuously from a viewpoint of further promoting stirring in a height direction in the liquid sample.

In the level difference 11, the height level of the bottom surface of the flow path 2 is changed, and a convex structure (for example, a protrusion) or a concave structure (for example, a groove) is removed.

The height of the bottom surface of the level difference 11 is higher on the downstream side than on the upstream side. In this case, the liquid sample is spread over the level difference 11 due to surface tension of the liquid sample, and at this time, stirring in the height direction is promoted in the liquid sample, and a reaction rate between the substance to be detected and the label is improved. Therefore, performance of the test kit is improved.

An amount of change in the height of the bottom surface level of the level difference 11 is preferably equal to or less than twice the height of the microstructure 8A on the upstream side of the level difference 11. In this case, advance of the liquid sample by the capillary force at the level difference 11 is performed more smoothly. Here, the height of the microstructure 8A is a height of the convex portion 8, for example.

The amount of change in the height of the bottom surface level of the level difference 11, that is, the height of the level difference 11 is equal to or more than 5 μm and equal to or less than 1000 μm, and preferably equal to or more than 10 μm and equal to or less than 500 μm.

In the region B on the downstream side of the level difference 11, an inclination may be provided such that the height level on the downstream side of the region B (for example, an opposite side 20B of a specific side 20A) approaches the height level on the upstream side (for example, the specific side 20A). The inclination is preferably provided toward the downstream side. In this case, the liquid sample in the flow path is easily developed by the influence of gravity, the reaction time can be shortened, and coloring of the background due to the remaining label after the development of the liquid sample can be suppressed.

With the level difference 11 as a boundary, the shape of the convex portion 8 may change. At the level difference 11, a change in a height of the liquid level of the developing liquid sample occurs. However, by changing the shape of the convex portion 8, contact between the microstructure and the liquid sample can be promoted, and sensitivity can be improved. The height of the liquid level height mentioned herein refer to a height from the bottom surface of the flow path to the liquid level of the developing liquid sample in each region. The shape of the convex portion 8 mentioned herein includes a size of the convex portion 8.

Specifically, the height of the liquid level immediately exceeding the level difference 11 is lower than the upstream side of the level difference. Therefore, although a flow amount of the liquid sample is reduced, the entire microstructure is brought into contact with the liquid sample with the level difference 11 as a boundary, contact between the microstructure and the substance to be detected in the liquid sample can be promoted, and sensitivity can be improved. With the level difference 11 as a boundary, in a case where the height of the microstructure on the downstream side of the level difference 11 is reduced, contact between the microstructure and the substance to be detected in the liquid sample can be further promoted, and sensitivity can be further improved. The flow rate mentioned herein refer to a volume of a liquid sample that has passed through a flow path section in a direction perpendicular to the developing direction of the liquid sample per unit time.

A height 6 of the convex portion 8 constituting the microstructure 7 is preferably equal to or more than 10 μm and equal to or less than 500 μm. The height 6 of the convex portion 8 may change within this range between a plurality of the convex portions 8 (may be different from one another). In a case where the height 6 of the convex portion 8 is equal to or more than 10 μm, the volume of the flow path 2 increases, and the liquid sample can be developed in a shorter time. In a case where the height 6 of the convex portion 8 is equal to or less than 500 μm, it is possible to reduce the time and the cost for preparing the microstructure 7, and preparation of the microstructure 7 becomes easier.

Figure 3A:
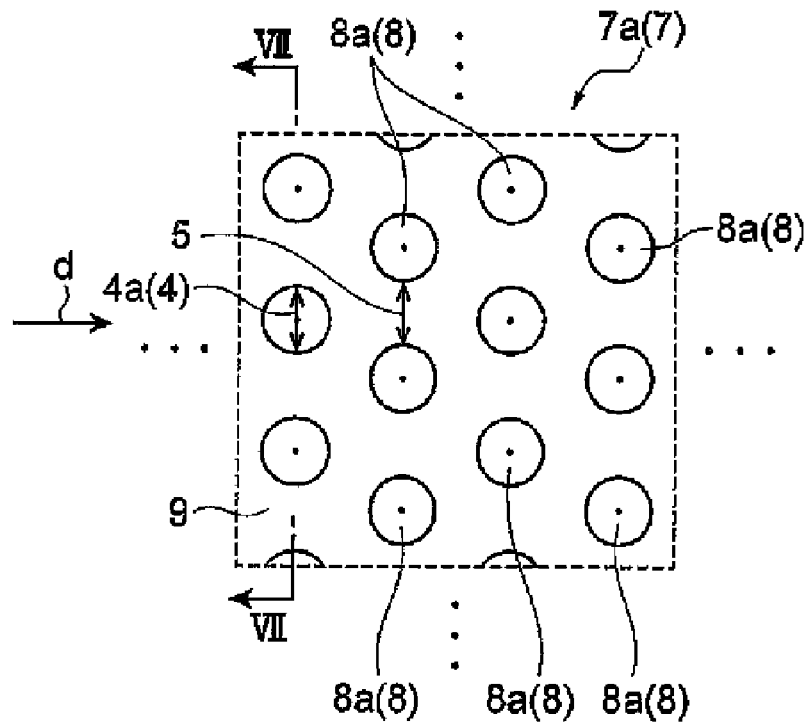
FIG. 3(a) is an example of an embodiment according to the present invention, and is a bird's-eye view (top view) of a microstructure.
Figure 3B:
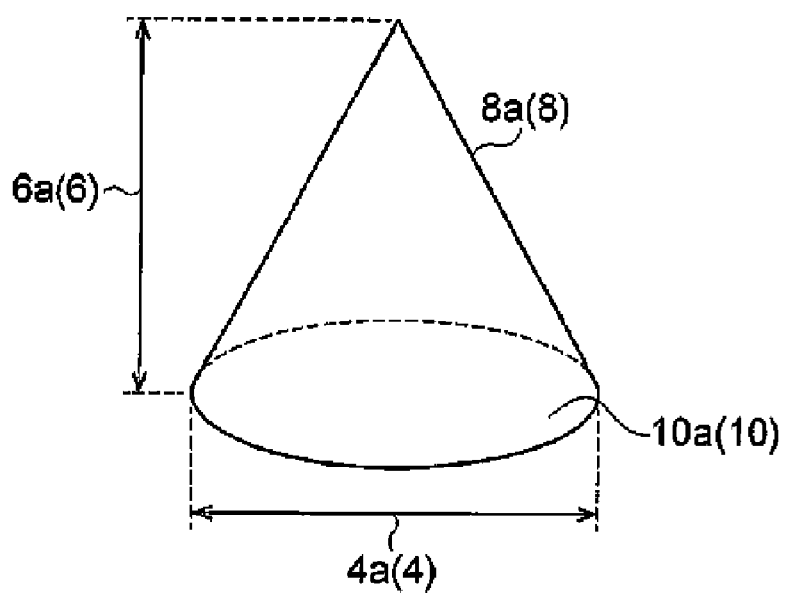
FIG. 3(b) is a perspective view of a convex portion constituting the microstructure illustrated in FIG. 3(a).
Figure 4A:
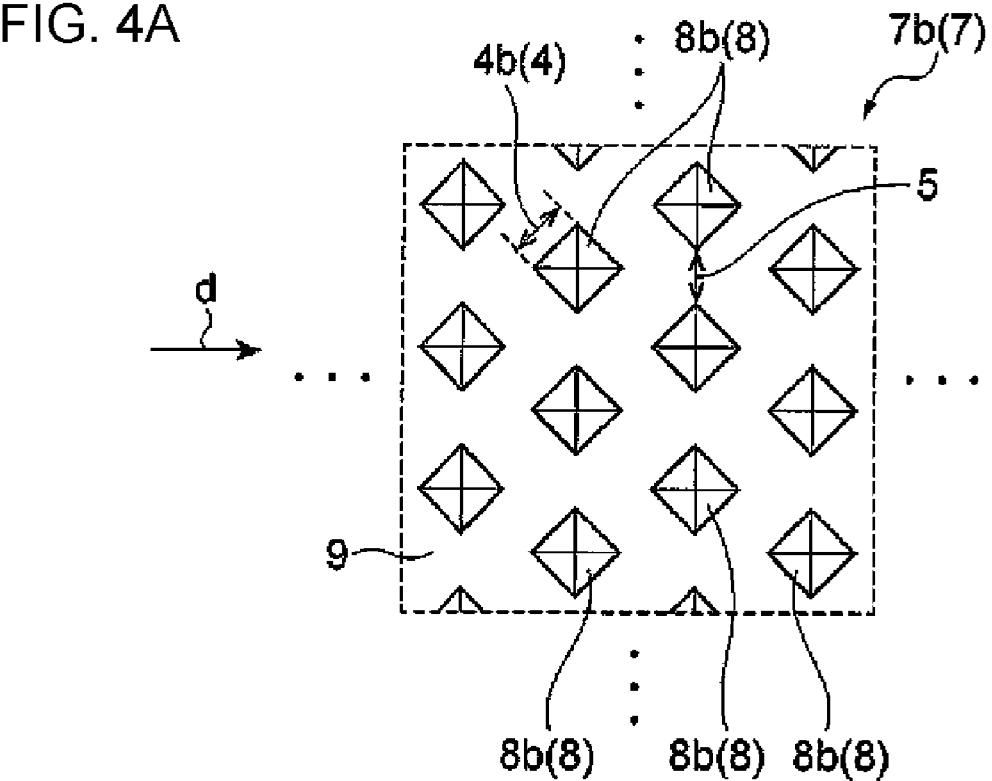
FIG. 4(a) is an example of an embodiment according to the present invention, and is a bird's-eye view (top view) of the microstructure.
Figure 4B:
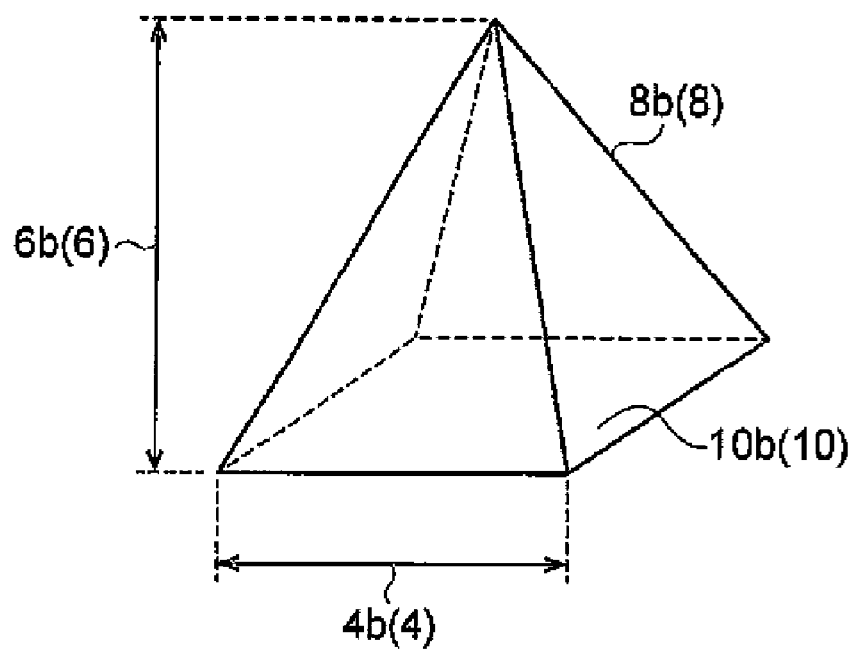
FIG. 4(b) is a perspective view of a convex portion constituting the microstructure illustrated in FIG. 4(a).
Figure 5A:
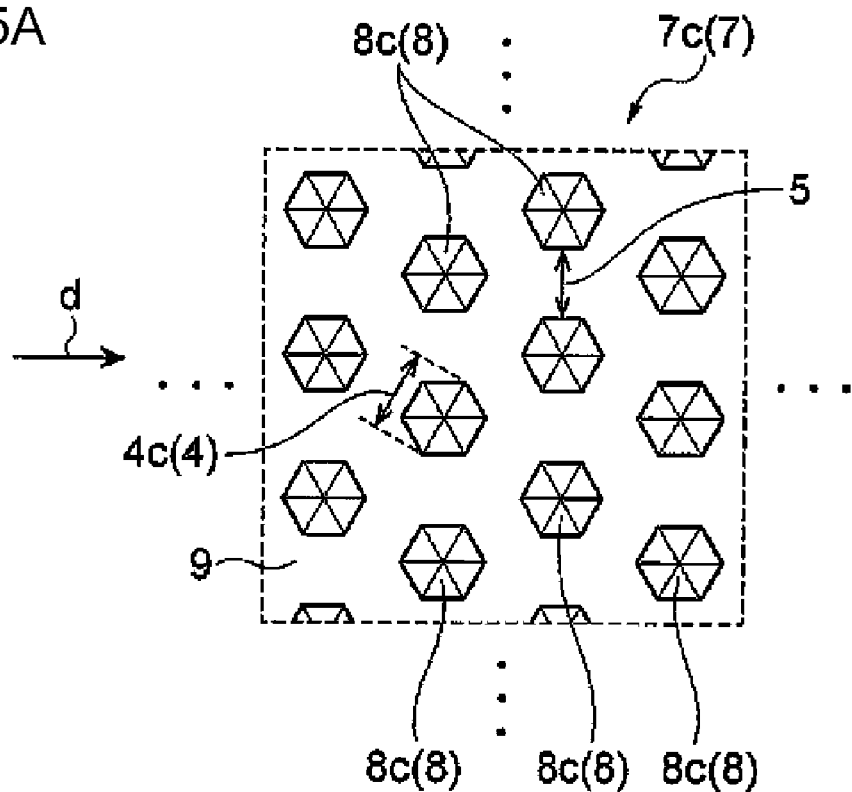
FIG. 5(a) is an example of an embodiment according to the present invention, and is a bird's-eye view (top view) of the microstructure.
Figure 5B:
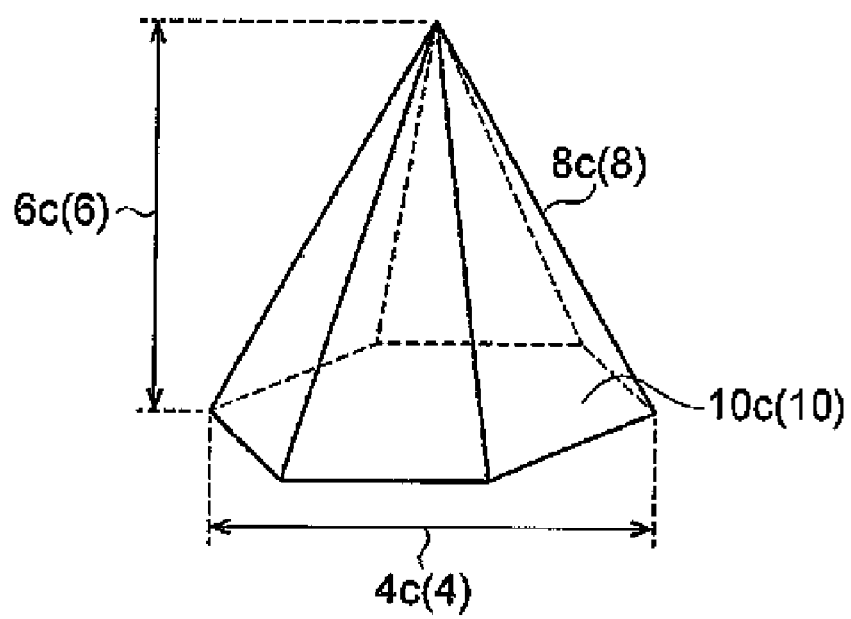
FIG. 5(b) is a perspective view of a convex portion constituting the microstructure illustrated in FIG. 5(a).
Figure 6A:
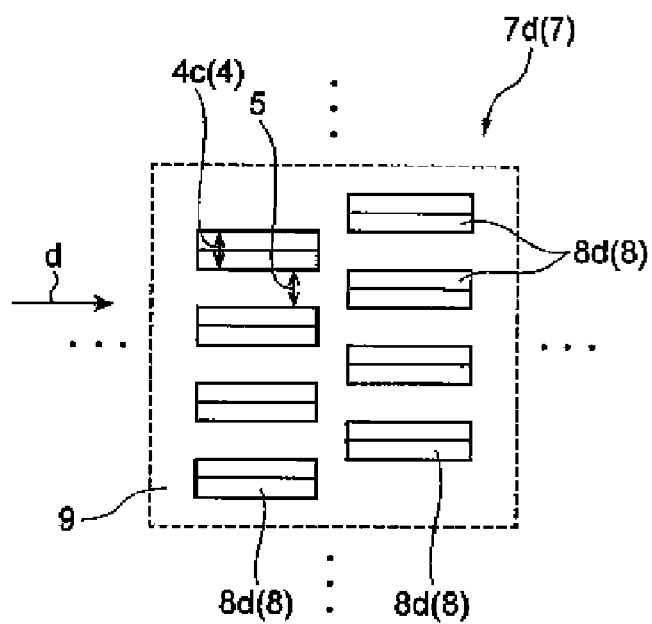
FIG. 6(a) is an example of an embodiment according to the present invention, and is a bird's-eye view (top view) of the microstructure.
Figure 6B:
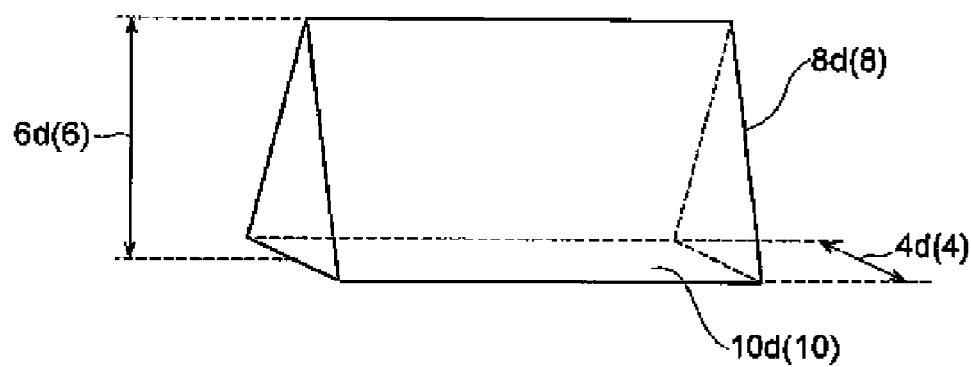
FIG. 6(b) is a perspective view of a convex portion constituting the microstructure illustrated in FIG. 6(b).
Figure 7:
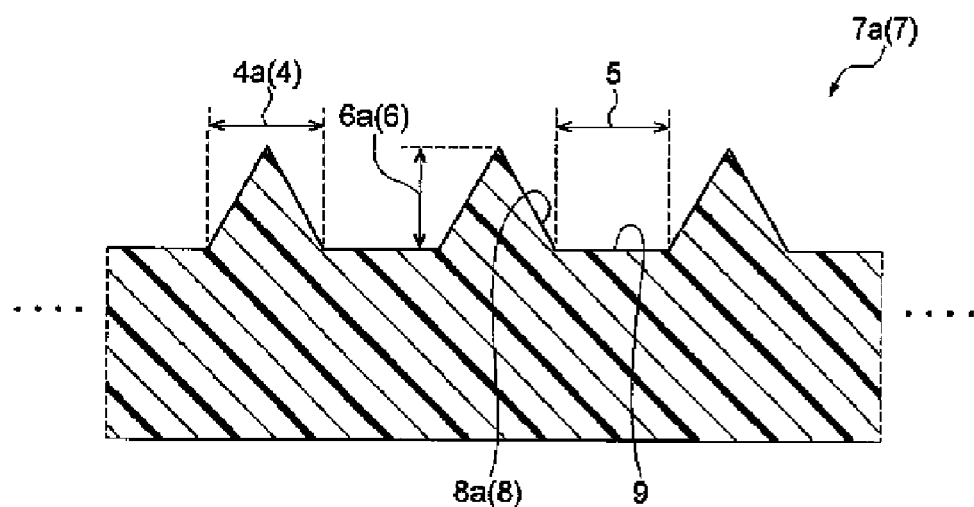
FIG. 7 is an example of an embodiment according to the present invention, and is a sectional view of a membrane carrier having the microstructure.

The height 6 of the convex portion 8 is defined as a maximum length of the convex portion 8 in a direction orthogonal to the flat portion 9. As illustrated in FIGS. 3(a), 3(b), and 7, in a case where the shape of the convex portion 8a is a cone, the height 6a of the convex portion 8a is the maximum length of the convex portion 8a in the direction orthogonal to the flat portion 9 (the height of the cone). As illustrated in FIGS. 4(a) and 4(b), in a case where the shape of the convex portion 8b is a quadrangular pyramid, the height 6b of the convex portion 8b is the maximum length of the convex portion 8b in the direction orthogonal to the flat portion 9 (height of the quadrangular pyramid). As illustrated in FIGS. 5(a) and 5(b), in a case where the shape of the convex portion 8c is a hexagonal pyramid, the height 6c of the convex portion 8c is the maximum length of the convex portion 8c in the direction orthogonal to the flat portion 9 (height of the hexagonal pyramid). As illustrated in FIGS. 6(a) and 6(b), in a case where the shape of the convex portion 8d is a horizontally placed triangular prism, the height 6d of the convex portion 8d is the maximum length of the convex portion 8d in the direction orthogonal to the flat portion 9 (height of the horizontally placed triangular prism).

A diameter 4 of the bottom surface 10 of the convex portion 8 is defined as a representative length of the bottom surface 10 of the convex portion 8. The representative length of the bottom surface 10 is a diameter in a case where the shape of the bottom surface 10 is a circle, a shortest side length in a case where the shape of the bottom surface 10 is a triangle or a quadrangle, a longest diagonal length in a case where the shape of the bottom surface 10 is a pentagon or more polygon, and a longest length on the bottom surface 10 in a case where the shape of the bottom surface 10 is another shape.

FIG. 7 is an arrow sectional view of the membrane carrier 3 having the microstructure 7a illustrated in FIG. 3 taken along the line VII-VII. As illustrated in FIGS. 3(a), 3(b), and 7, in a case where the shape of the convex portion 8a is a cone, the diameter 4a of the bottom surface 10a of the convex portion 8a is a diameter of the bottom surface (circle) of the cone. As illustrated in FIGS. 4(a) and 4(b), in a case where the shape of the convex portion 8b is a regular quadrangular pyramid, the diameter 4b of the bottom surface 10b of the convex portion 8b is a length of the side of the bottom surface (square) 10b. As illustrated in FIGS. 5(a) and 5(b), in a case where the shape of the convex portion 8c is a regular hexagonal pyramid, the diameter 4c of the bottom surface 10c of the convex portion 8c is the length of a diagonal passing through the center of the bottom surface (regular hexagon) 10c (the length of the longest diagonal). As illustrated in FIGS. 6(a) and 6(b), in a case where the shape of the convex portion 8d is a horizontally disposed triangular prism, the diameter 4d of the bottom surface 10d of the convex portion 8d is a length of the shortest side of the bottom surface (rectangle) 10d (in FIGS. 6(a) and 6(b), the length in the direction orthogonal to the transporting direction d of the liquid sample).

A bottom area of the convex portion 8 (the area per one bottom surface 10 of the convex portion 8) constituting the microstructure 7 is preferably equal to or more than 75 $\mu m^2$ and equal to or less than 250,000 $\mu m^2$. The bottom area of the convex portion 8 may change within this range between the plurality of convex portions 8 (may be different from one another). In a case where the bottom area of the convex portion 8 is equal to or more than 75 $\mu m^2$, fine processing becomes easy, and the cost of preparing a microstructure is further reduced. In a case where the bottom area of the convex portion 8 is equal to or less than 250,000 $\mu m^2$, the number of the convex portions 8 constituting the microstructure 7 in one test kit increases, and the development of the liquid sample becomes easier.

A closest distance 5 between the convex portions 8 constituting the microstructure 7 is preferably equal to or less than 500 μm, and more preferably equal to or more than 2 μm and equal to or less than 100 μm. The closest distance 5 between the convex portions 8 may change within this range between the plurality of convex portions 8 (may be different from one another). The closest distance 5 between the convex portions 8 cannot be less than 0 μm, and in a case where the closest distance 5 between the convex portions 8 is equal to or less than 500 μm, the contact area between the liquid sample and the flow path 2 increases. With this, the capillary force increases, and moving the liquid sample becomes easier. Here, "the closest distance between the convex portions 8" is the closest distance between a pair of adjacent convex portions 8 in the same region.

An aspect ratio of the convex portion 8 constituting the microstructure 7 is preferably equal to or more than 0.1 and equal to or less than 2.0. The aspect ratio mentioned herein is a value (Lh/Lv) obtained by dividing the height 6 (Lh) of the convex portion 8 by the representative length (diameter 4) (Lv) of the bottom surface 10 of the convex portion 8. In a case where the aspect ratio is equal to or more than 0.1, the contact area between the liquid sample and the flow path 2 increases, and with this, the capillary force increases, thereby making it easier to move the liquid sample. In a case where the aspect ratio is equal to or less than 2.0, preparation of a microstructure becomes easier.

The microstructure 7 may be formed of convex portions 8 the same as one another in the same region. The microstructure 7 may be formed of convex portions 8 different from one another in the same region. In this case, the convex portions 8 different from one another may be arranged in the same region in accordance with a certain rule along the transporting direction d of the liquid sample. That is, in the same region, the convex portion 8 may be, for example, arranged in line such that at least one of the diameter 4 of the bottom surface 10 of the convex portion 8, the height 6 of the convex portion 8, the closest distance 5 between the convex portions 8, and the aspect ratio of the convex portion 8 (height 6/diameter 4) may change (increase or decrease) along the transporting direction d of the liquid sample in accordance with a certain rule.

Figure 10:
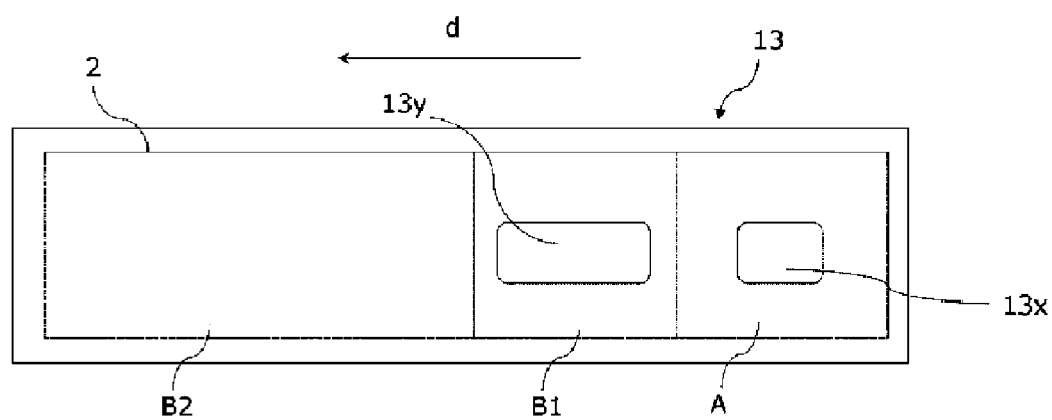
FIG. 10 is an example of an embodiment according to the present invention, and is a schematic top view of a membrane carrier.

FIG. 10 is a top view of a membrane carrier according to another embodiment. In the membrane carrier 3 illustrated in FIG. 2, the detection zone 3y is provided in the region B, but in the membrane carrier 13 illustrated in FIG. 10, the detection zone 13y is provided in the region B1. As illustrated in FIG. 10, the dropping zone 13x and the detection zone 13y may be formed over substantially the entirety of the membrane carrier 13 in a short-side direction.

The microstructure 7 and the membrane carrier 3 of the liquid sample test kit 18 of the present embodiment may be made of thermoplastic plastic. In other words, it is possible to prepare the membrane carrier 3 having the microstructure 7 by processing a membrane-shaped substrate formed of thermoplastic plastic. Examples of a processing method include thermal imprinting, UV imprinting, injection molding, etching, photolithography, mechanical cutting, and laser processing, for example. Among these, as a technique of performing accurate processing at a low cost, thermal imprinting on thermoplastic plastic is suitable. Examples of the thermoplastic plastic include a polyester resin, a polyolefin resin, a polystyrene resin, a polycarbonate resin, a fluorine resin, an acrylic resin, and the like. Specifically, it is possible to use various thermoplastic plastics such as polyethylene terephthalate (PET), cycloolefin polymer (COP), polypropylene (PP), polystyrene (PS), polycarbonate (PC), polyvinylidene fluoride (PVDF), and polymethyl methacrylate (PMMA).

In a case of a processing method using a mold such as imprinting or injection molding, the conical body has a smaller upper portion than the bottom surface. Therefore, a volume to be carved out is smaller at a time of preparing a mold than preparing a column with the same bottom surface, and the mold can be prepared at a preparation is smaller than production is smaller than that of a column with the same bottom. And the mold can be manufactured at a low cost. In this case, it is possible to perform detection of the substance to be detected in the liquid sample at a lower cost.

As described above, the membrane carrier 3 is a membrane carrier 3 for a liquid sample test kit 18 that detects the substance to be detected in the liquid sample, and the membrane carrier 3 includes the microstructure 7 that causes capillary action for transporting the liquid sample, provided on one surface of the membrane carrier 3, the flow path 2 that transports the liquid sample, formed by the microstructure 7, and the level difference 11 at which the height level of the bottom surface of the flow path 2 changes.

In the liquid sample test kit 18 according to the present embodiment, a change in color occurs at a time when the substance to be detected is detected in the detection zone 3y of the membrane carrier 3. The change in color may be a change in color that can be confirmed by an optical technique.

Examples of the optical technique mainly include two techniques of visual determination and measurement of fluorescence intensity. In a case of visual determination, change in color preferably occurs in a case where color difference between two color stimuli at a time of measuring color before and after the detection by a color system of the CIE1976L*a*b* color space (A E described in JIS Z8781-4: 2013) is equal to or more than 0.5. In a case where the color difference is equal to or more than 0.5, it is easy to visually confirm the color difference. In a case where the fluorescence intensity is measured and determined, the change in color preferably occurs such that a ratio (FI1/FI2) of fluorescence intensity (FI1) in the detection zone 3y and fluorescence intensity (FI2) in an upstream region and a downstream region adjacent to the detection zone 3y=10/1 or more. In a case where the ratio is equal to or more than 10/1, separation of signal and noise becomes easy.

In order to prepare the detection zone 3y in the liquid sample test kit 18 of the present embodiment, in an embodiment, a detection substance is immobilized on at least a part of the flow path 2. That is, the detection substance that detects the substance to be detected is immobilized in the detection zone 3y. The change in color in the detection zone 3y is caused by holding the substance to be detected in the detection zone 3y by the detection substance (reacting with the detection substance).

In other words, the method of manufacturing the liquid sample test kit 18 includes immobilizing the detection substance in the detection zone 3y. As the detection substance, a detection substance that causes a change in color by holding the substance to be detected in the detection zone 3y is preferable. From a viewpoint that the detection substance (reagent) can be more efficiently immobilized in the detection zone 3y, pre-surface treatment may be performed in a site provided with the detection zone 3y in the membrane carrier 3.

The method of the surface treatment is not particularly limited, and various methods such as UV irradiation, UV/ozone treatment, various plasma treatments, and surface modification with 3-aminopropyl triethoxysilane or glutaraldehyde can be used.

In the present embodiment, examples of the detection substance (reagent) include an antibody, for example. The antibody is an antibody that reacts with the substance to be detected by an antigen-antibody reaction, and may be a polyclonal antibody or a monoclonal antibody.

The change in color in the detection zone 3y may be caused by a label having an antibody or an antigen-binding fragment thereof that specifically reacts with the substance to be detected in the liquid sample. The change in color occurs as the label is held in the detection zone 3y by the detection substance (reacts (binds) with the detection substance) and colored, for example.

The label may be one in which the antibody or antigen-binding fragment thereof is bound to particles such as colloidal particles and latex particles, for example. The antigen-binding fragment refers to a fragment that can specifically bind to a substance to be detected, for example, an antigen-binding fragment of an antibody. The label can bind to the substance to be detected via an antibody or an antigen-binding fragment thereof. The particles may have magnetism or fluorescent properties. Examples of the colloidal particles include metal colloidal particles such as gold colloidal particles and platinum colloidal particles. The particles are preferably latex particles in view of particle diameter control, dispersion stability, and binding easiness. Although the material of the latex particles is not particularly limited, polystyrene is preferable.

The particles are preferably colored particles or fluorescent particles, and more preferably colored particles in view of visibility. The colored particles may be any particles as long as the color can be detected with naked eye. The fluorescent particles may contain a fluorescent substance. The particles may be colored latex particles or fluorescent latex particles. In a case where the particles are colored latex particles, the change in color is suitably determined visually. In a case where the particles are fluorescent latex particles, the change in color is suitably determined by measuring the fluorescence intensity.

The label is provided in at least a part of the test kit 18 so as to react with the substance to be detected in the dropped liquid sample. For example, the label may be provided in a member in the test kit 18 or may be provided in at least a part (upstream side from the detection zone 3y) of the flow path 2 of the membrane carrier 3. The label that has reacted (bound) with the substance to be detected is held in the detection zone 3y by the detection substance (by the detection substance reacting (binding) with the substance to be detected). With this, a change in color (coloring by the label) occurs in the detection zone 3y.

The detection zone 3y may be provided on an inclined portion on the downstream side of the level difference 11. In the inclined portion, the liquid sample in the flow path is easily developed due to the influence of gravity, and the suppression of the coloring of the background by the remaining label after the development of the liquid sample becomes particularly remarkable. Therefore, the change in color in the detection zone 3y is particularly easily recognized, and the detection sensitivity of the substance to be detected is improved.

The test method of the liquid sample according to an aspect of the present embodiment is a test method using the test kit 18.

A test method of a liquid sample using the test kit 18 may include mixing a liquid sample and a label specifically binding to a substance to be detected in the liquid sample, preparing a mixture liquid sample (mixed liquid sample), and binding the substance to be detected and the label to each other; dropping the mixture liquid sample onto a dropping zone 3x provided in the membrane carrier 3; transporting the mixture liquid sample from the dropping zone 3x to the detection zone 3y by the microstructure 7; and detecting a change in color (development of color of the label) in the detection zone 3y.

For example, the test method may include dropping the liquid sample onto the dropping zone 3x on the surface of the membrane carrier 3; transporting the liquid sample from the dropping zone 3x to the detection zone 3y through the microstructure 7 by the capillary action by the microstructure 7 (a plurality of convex portions 8) formed on the surface of the membrane carrier 3; and detecting a change in color in the detection zone 3y (optically determining the presence or absence of a change in color) by binding the substance to be detected in the liquid sample to a label via the antibody or antigen-binding fragment thereof, and binding the substance to be detected to a reagent immobilized on the detection zone 3y, in the transporting process.

In binding the substance to be detected and the label to each other of the test method, the method of mixing the liquid sample with the label is not particularly limited. For example, the method may be a method of adding a liquid sample to a container containing the label, for example, a method of mixing a liquid containing the label with the liquid sample. For example, a filter may be interposed between dropping ports of the container containing the liquid sample, and the label may be immobilized in the filter.

EXAMPLES

Hereinafter, the present embodiment will be specifically described, but the present embodiment is not limited to these experimental examples.

Experimental Example 1

<Preparation of Mold>

Figure 11:
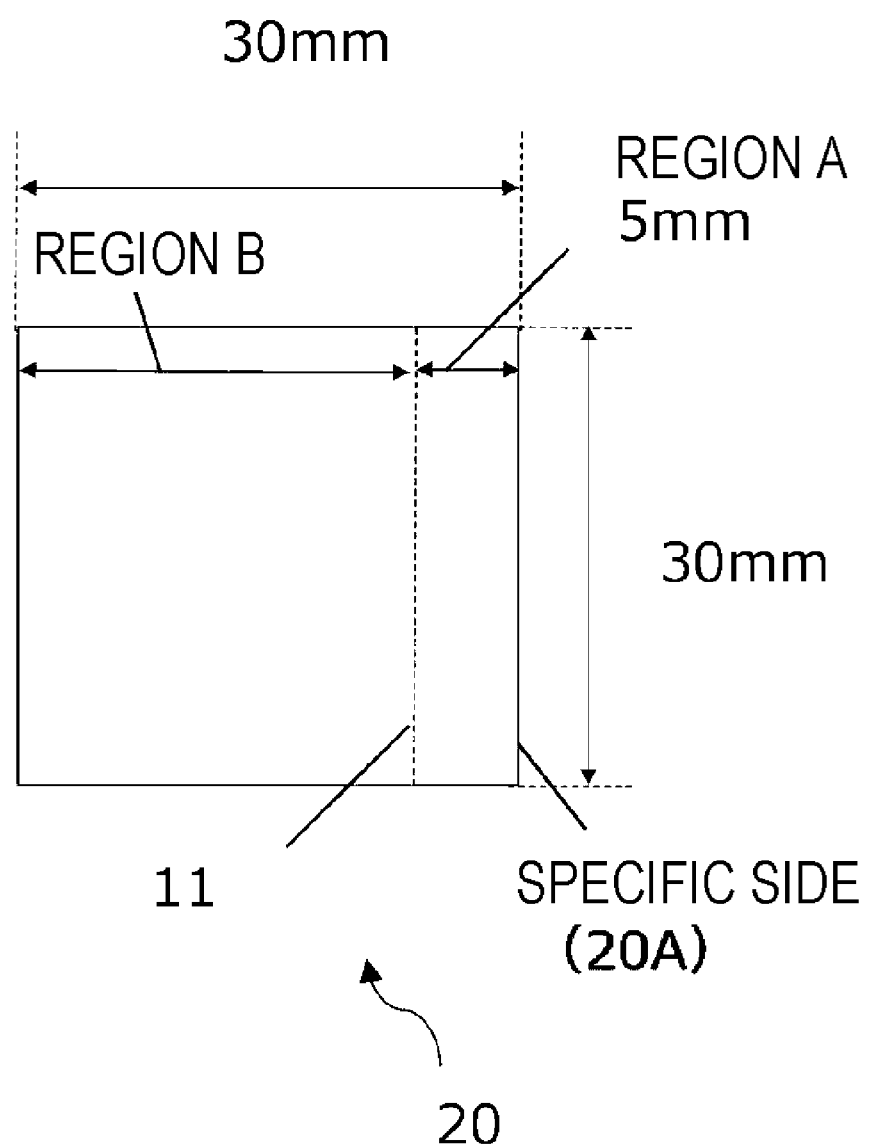
FIG. 11 is an example of an embodiment according to the present invention, and is a schematic view of a mold for forming a microstructure.

A mold was prepared by laser processing and mechanical cutting. FIG. 11 illustrates a mold 20 for preparing a microstructure. The mold 20 illustrated in FIG. 11 has a plurality of regions (a first region A and a second region B), and a concave portion corresponding to the microstructure (a convex portion) illustrated in FIG. 8 is formed on the surface (not illustrated). The mold 20 is made of an aluminum alloy A5052. At the center of the mold (die), fine processing is performed in a range of 30 mm×30 mm. Within a processing range of the mold 20, a level difference 11 having a depth (height) of 100 µm is provided in parallel with a specific side (20A) at a position of 5 mm in the processing range from the specific side (20A). In a region (region A) between the level difference and the specific side (20A) and a region (region B) other than the region A, a conical concave portion (a concave portion capable of forming a convex portion at a time of transferring the microstructure) having a diameter of 100 µm and a depth (also referred to as height in the table) of 100 µm is arranged in line in a triangular arrangement form of FIGS. 3(a), 3(b), and 8 with the closest distance between the microstructures (distance between the closest microstructures) 5 set to 5 µm.

A mold release treatment was performed on an irregular surface of the mold in order to easily and reliably peel off the mold at a time of transfer from thermoplastic plastic. The mold release treatment was performed by performing immersion in Optool HD-2100TH manufactured by Daikin Industries, Ltd. for about 1 minute, drying, and then allowing to stand overnight.

<Transfer of Microstructure>

The microstructure was transferred to a thermoplastic plastic using the mold obtained as described above. As the thermoplastic plastic, polystyrene (Denka Styrene sheet manufactured by Denka Corporation, film thickness 300 µm) was used. Thermal imprinting was used as a processing method, and X-300 manufactured by SCIVAX was used as an apparatus. At a molding temperature of 120° C. and an applied pressure of 5.5 MPa, transfer was performed for 10 minutes. After the transfer, the thermoplastic plastic and the mold were cooled to 80° C. while applying pressure, and then the pressure was removed to prepare a membrane carrier having a region A and a region B in order from one end side.

Experimental Example 2

Except that the depth of the level difference in Experimental Example 1 was 10 µm, and the microstructures in the region A and the region B were conical concave portions having a diameter of 10 µm and a depth of 10 µm, a membrane carrier was prepared under the same conditions as in Experimental Example 1.

Experimental Example 3

Except that the depth of the level difference in Experimental Example 1 was 500 µm, and the microstructures in the region A and the region B were conical concave portions having a diameter of 500 µm and a depth of 500 µm, a membrane carrier was prepared under the same conditions as in Experimental Example 1.

Experimental Example 4

Except that the depth of the level difference in Experimental Example 1 was 50 µm, a membrane carrier was prepared under the same conditions as in Experimental Example 1.

Experimental Example 5

Except that the depth of the level difference in Experimental Example 1 was 200 µm, a membrane carrier was prepared under the same conditions as in Experimental Example 1.

Experimental Example 6

Except that the microstructure of the region B in Experimental Example 1 was a conical concave portion having a diameter of 10 µm and a depth of 10 µm, a membrane carrier was prepared under the same conditions as in Experimental Example 1.

Experimental Example 7

Except that the depth of the level difference in Experimental Example 1 was 500 µm and the microstructure of the region A was a conical concave portion having a diameter of 500 µm and a depth of 500 µm, a membrane carrier was prepared under the same conditions as in Experimental Example 1.

Experimental Example 8

Except that the depth of the level difference in Experimental Example 1 was 500 µm, the microstructure of the region A was a conical concave portion having a diameter of 500 µm and a depth of 500 µm, and the microstructure of the region B was a conical concave portion having a diameter of 10 µm and a depth of 10 µm, a membrane carrier was prepared under the same conditions as in Experimental Example 1.

Experimental Example 9

Figure 12:
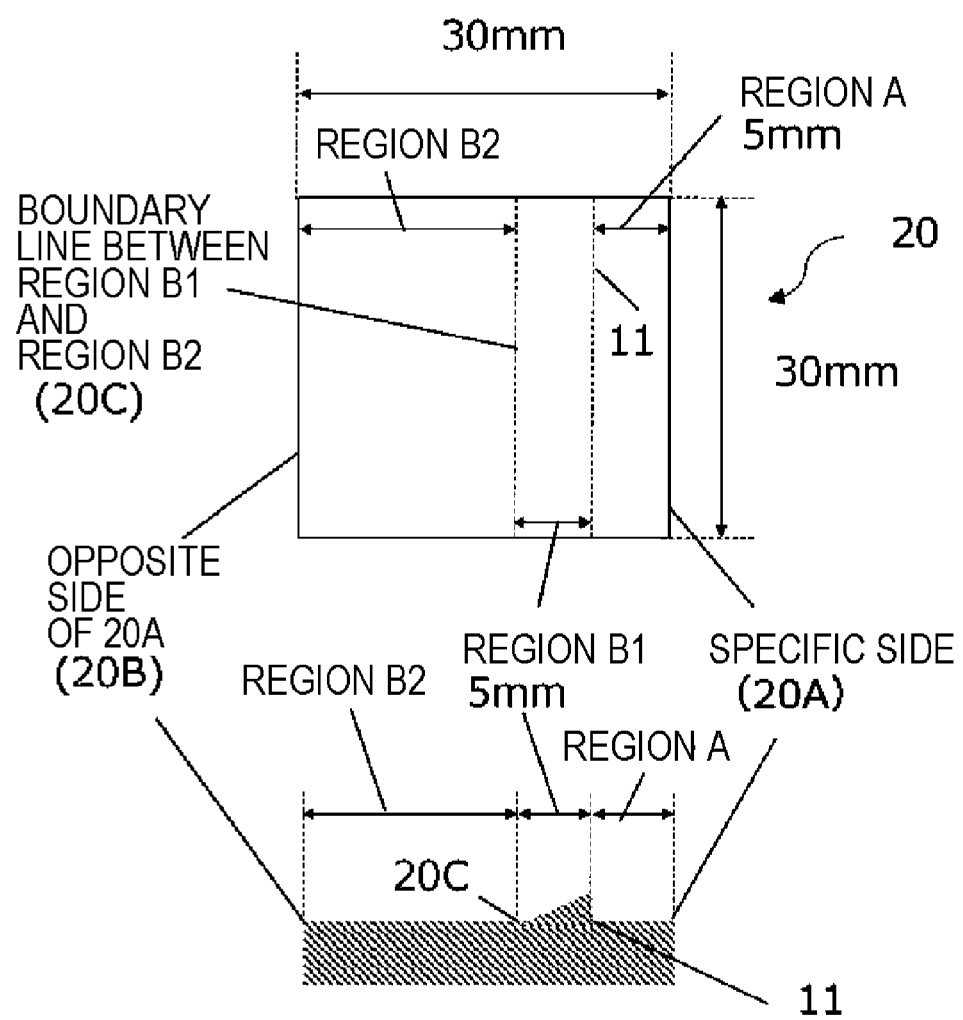
FIG. 12 is an example of an embodiment of the present invention, and is a schematic view (top view, sectional view) of a mold for forming a microstructure.

FIG. 12 illustrates a mold 20 for preparing the microstructure of the Experimental Example 9. Unless otherwise specified, it is the same as the mold 20 of Experimental Example 1. FIG. 12 does not illustrate a concave portion corresponding to the microstructure (convex portion). In the region B, an inclination is provided in a region (region B1) having a width of 5 mm in a direction opposite to the specific side 20A from the level difference 11, and the height level of the mold surface in a region (region B2) other than the region B1 in the region B was matched with the height level of the mold surface of the region A, a membrane carrier was prepared under the same conditions as in Experimental Example 1. However, the height level of the specific side 20A, the height level of the opposite side 20B of the specific side 20A, and the height level of a boundary line 20C between the region B1 and the region B2 were the same.

Experimental Example 10

Except that the depth of the level difference in Experimental Example 9 was 50 µm, a membrane carrier was prepared under the same conditions as in Experimental Example 9.

Experimental Example 11

Except that the depth of the level difference in Experimental Example 9 was 200 µm, a membrane carrier was prepared under the same conditions as in Experimental Example 9.

Experimental Example 12

Except that the microstructures of the region B1 and the region B2 in Experimental Example 9 were conical concave portions having a diameter of 10 µm and a depth of 10 µm, a membrane carrier was prepared under the same conditions as in Experimental Example 9.

Experimental Example 13

Except that the depth of the level difference in Experimental Example 9 was 500 µm, and the microstructure of the region A was a conical concave portion having a diameter of 500 µm and a depth of 500 µm, a membrane carrier was prepared under the same conditions as in Experimental Example 9.

Experimental Example 14

Except that the depth of the level difference in Experimental Example 9 was 500 µm, the microstructure of the region A was a conical concave portion having a diameter of 500 µm and a depth of 500 µm, and the microstructures of the region B1 and the region B2 were conical concave portions having a diameter of 10 µm and a depth of 10 µm, a membrane carrier was prepared under the same conditions as in Experimental Example 9.

Experimental Example 15

Except that the microstructure of the region B1 in Experimental Example 9 was a conical concave portion having a diameter of 10 µm and a depth of 10 µm, a membrane carrier was prepared under the same conditions as in Experimental Example 9.

Experimental Example 16

Except that the depth of the level difference in Experimental Example 9 was 500 µm, and the microstructures of the region A and the region B2 were conical concave portions having a diameter of 500 µm and a depth of 500 µm, a membrane carrier was prepared under the same conditions as in Experimental Example 9.

Experimental Example 17

The depth of the level difference in Experimental Example 9 was 500 µm, the microstructures of the region A and the region B2 were conical concave portions having a diameter of 500 µm and a depth of 500 µm, and the microstructure of the region B1 was a conical concave portion having a diameter of 10 µm and a depth of 10 µm, a membrane carrier was prepared under the same conditions as in Experimental Example 9.

Experimental Example 18

Except that a level difference was not provided in the fine processing range of the mold, and a conical concave portion having a diameter of 100 µm and a depth of 100 µm was provided over the entire range of 30 mm×30 mm, a membrane carrier was produced under the same conditions as in Experimental Example 1.

Experimental Example 19

Except that the height level of the bottom surface was lower by 100 µm on the downstream side than on the upstream side of the level difference, a membrane carrier was prepared under the same conditions as in Experimental Example 1.

Experimental Example 20

Except that the depth of the level difference was 300 µm, a membrane carrier was prepared under the same conditions as in Experimental Example 9.

<Preparation of Detection Zone>

In the region B of the membrane carrier prepared as described above, a region corresponding to a width of 5 mm (region B1 in a structure having an inclination) in a direction opposite to a specific side (20A) from the level difference 11 was subjected to UV treatment. An anti-type A influenza NP antibody suspension and an anti-type B influenza NP antibody suspension were each applied to the portion at a line width of 1 mm (application amount: 3 µL each), dried well in warm air, and the detection substance was immobilized.

<Set of Labels>

Purified anti-type A influenza virus NP antibody (another antibody as described above) and purified anti-type B influenza virus NP antibody (another antibody as described above) were used. The anti-type A influenza virus NP antibody was covalently labeled with blue latex particles (manufactured by CM/BL Seradyne) having a particle size of 0.394 µm, suspended in a tris buffer containing saccharide, surfactant, and protein such that a concentration of latex particles was 0.025 w/v % to prepare containing saccharide, surfactant and protein, and sonicated to prepare a sufficiently dispersed and floated anti-type A label. Similarly, an anti-type B label in which blue latex particles were labeled with an anti-type B influenza virus NP antibody was prepared.

The anti-type A label and the anti-type B label were mixed with each other. Regarding the mixture obtained by mixing, an amount of 50 µL per square centimeter was applied to glass fiber (33GLASS NO. 10539766 manufactured by Schleicher & Schuell) having a size of 3 cm×1 cm, and dried well under warm air to prepare a label pad. Thereafter, the label pad was overlapped only at an end of 2 mm of the region A of the membrane carrier prepared as in Experimental Examples 1 to 20, and cut into strips having a width of 5 mm with a cutter to prepare an integrated liquid sample test kit.

<Detection Evaluation>

100 μL of the liquid sample was dropped on the label pad (dropping zone) at the end of the liquid sample test kit prepared as described above. As a liquid sample, using a specimen suspension attached to QuickNavi-Flu manufactured by Denka Seiken Co., Ltd. as a dilution solution, two kinds of a $4\times10^4$-fold diluted type A influenza virus A/Beijing/32/92 (H3N2) (hereinafter, referred to as type A in some cases) and a $4\times10^3$-fold diluted type B influenza virus B/Shangdong/7/97 (hereinafter, referred to as type B in some cases) were used.

TABLE 1

|  | Example 1 | Example 2 | Example 3 | Example 4 | Example 5 | Example 6 | Example 7 | Example 8 |
|---|---|---|---|---|---|---|---|---|
| Microstructure height of region A (μm) | 100 | 10 | 500 | 100 | 100 | 100 | 500 | 500 |
| Microstructure diameter of region A (μm) | 100 | 10 | 500 | 100 | 100 | 100 | 500 | 500 |
| Microstructure height of region B (μm) | 100 | 10 | 500 | 100 | 100 | 10 | 100 | 10 |
| Microstructure diameter of region B (μm) | 100 | 10 | 500 | 100 | 100 | 10 | 100 | 10 |
| Height of level difference (μm) | 100 | 10 | 500 | 50 | 200 | 100 | 500 | 500 |
| Limit magnification at which type A visual determination is possible | $7 \times 10^4$ | $7 \times 10^4$ | $6 \times 10^4$ | $6 \times 10^4$ | $7 \times 10^4$ | $8 \times 10^4$ | $7 \times 10^4$ | $7 \times 10^4$ |
| Limit magnification at which type B visual determination is possible | $7 \times 10^3$ | $7 \times 10^3$ | $6 \times 10^3$ | $6 \times 10^3$ | $7 \times 10^3$ | $8 \times 10^3$ | $7 \times 10^3$ | $7 \times 10^3$ |
| Time until density is stabilized (minute) | 6 | 7 | 5 | 5 | 7 | 7 | 6 | 7 |
| Comprehensive evaluation | A | B | B | B | B | A | A | B |
| Notes | Working Example | Working Example | Working Example | Working Example | Working Example | Working Example | Working Example | Working Example |

TABLE 2

|  | Example 9 | Example 10 | Example 11 | Example 12 | Example 13 | Example 14 | Example 15 |
|---|---|---|---|---|---|---|---|
| Microstructure height of region A (μm) | 100 | 100 | 100 | 100 | 500 | 500 | 100 |
| Microstructure diameter of region A (μm) | 100 | 100 | 100 | 100 | 500 | 500 | 100 |
| Microstructure height of region B1 (μm) | 100 | 100 | 100 | 10 | 100 | 10 | 10 |
| Microstructure diameter of region B1 (μm) | 100 | 100 | 100 | 10 | 100 | 10 | 10 |
| Microstructure height of region B2 (μm) | 100 | 100 | 100 | 10 | 100 | 10 | 100 |
| Microstructure diameter of region B2 (μm) | 100 | 100 | 100 | 10 | 100 | 10 | 100 |
| Height of level difference (μm) | 100 | 50 | 200 | 100 | 500 | 500 | 100 |
| Limit magnification at which type A visual determination is possible | $7 \times 10^4$ | $6 \times 10^4$ | $7 \times 10^4$ | $8 \times 10^4$ | $7 \times 10^4$ | $7 \times 10^4$ | $8 \times 10^4$ |
| Limit magnification at which type B visual determination is possible | $7 \times 10^3$ | $6 \times 10^3$ | $7 \times 10^3$ | $8 \times 10^3$ | $7 \times 10^3$ | $7 \times 10^3$ | $8 \times 10^3$ |
| Time until density is stabilized (minute) | 5 | 4 | 6 | 6 | 5 | 7 | 6 |
| Comprehensive evaluation | A | B | A | A | A | B | A |
| Notes | Working Example | Working Example | Working Example | Working Example | Working Example | Working Example | Working Example |

|  | Example 16 | Example 17 | Example 18 | Example 19 | Example 20 |
|---|---|---|---|---|---|
| Microstructure height of region A (μm) | 500 | 500 | 100 | 100 | 100 |
| Microstructure diameter of region A (μm) | 500 | 500 | 100 | 100 | 100 |
| Microstructure height of region B1 (μm) | 100 | 10 | 100 | 100 | 100 |

TABLE 2-continued

|  |  |  |  |  |  |
|---|---|---|---|---|---|
| Microstructure diameter of region B1 (μm) | 100 | 10 | 100 | 100 | 100 |
| Microstructure height of region B2 (μm) | 500 | 500 | 100 | 100 | 100 |
| Microstructure diameter of region B2 (μm) | 500 | 500 | 100 | 100 | 100 |
| Height of level difference (μm) | 500 | 500 | 0 | −100 | 300 |
| Limit magnification at which type A visual determination is possible | $7 \times 10^4$ | $7 \times 10^4$ | $4 \times 10^4$ | Liquid remains on upstream side of level difference | $7 \times 10^4$ |
| Limit magnification at which type B visual determination is possible | $7 \times 10^3$ | $7 \times 10^3$ | $4 \times 10^3$ | Liquid remains on upstream side of level difference | $7 \times 10^3$ |
| Time until density is stabilized (minute) | 4 | 7 | 5 | Liquid does not flow to downstream side and measurement is not possible | 10 |
| Comprehensive evaluation | A | B | D | D | C |
| Notes | Working Example | Working Example | Comparative Example | Comparative Example | Working Example |

In Example 19, the height level of the bottom surface was lower by 100 μm on the downstream side than on the upstream side of the level difference.

The determination of the detection was performed by visually observing the presence or absence of a colored line in the detection zone (the type A influenza virus detection portion and the type B influenza virus detection portion) after 15 minutes.

As a result of the determination, in a case where a solution obtained by diluting A/Beijing/32/92 (H3N2) by $4 \times 10^4$ was used, a change in color was confirmed only in the type A detection zone, and in a case where a solution obtained by diluting B/Shangdong/7/97 by $4 \times 10^3$ was used, a change in color was confirmed only in the type B detection zone.

From the membrane carrier prepared as in Experimental Examples 1 to 20, a liquid sample test kit was prepared as described above. Subsequently, in a case where a dilution rate of the type A influenza virus A/Beijing/32/92 (H3N2) was increased from $4 \times 10^4$, a dilution rate (type A limit magnification at which visual determination is possible), at which the presence or absence of a colored line could not be visually observed 15 minutes after the start of the test, was obtained. In a case of performing test at a dilution rate of 1/2 of the dilution rate, a time from the start of the test to the color density of the colored line was stabilized (time until the type A density was stabilized) was obtained. The result is shown in Tables 1 and 2.

From the membrane carrier prepared as in Experimental Examples 1 to 20, a liquid sample test kit was prepared as described above. Subsequently, in a case where a dilution rate of the type B influenza virus B/Shangdong/7/97 was increased from $4 \times 10^3$, a dilution rate (type B limit magnification at which visual determination is possible), at which the presence or absence of a colored line could not be visually observed, was obtained. In a case of performing test at a dilution rate of 1/2 of the dilution rate, a time from the start of the test to the color density of the colored line was stabilized (time until the type B density was stabilized) was obtained. The result is shown in Tables 1 and 2.

As for the time until the density is stabilized, an average value of a time until the type A density is stabilized and a time until the type B density is stabilized was used as a time until the density is stabilized.

Tables 1 and 2 also show the results of the comprehensive evaluation based on the following criteria for each experimental example.

A: Those that can be determined at a dilution rate of equal to or more than $7 \times 10^4$ for type A and at a dilution rate of equal to or more than $7 \times 10^3$ for type B, or those that can be determined at a dilution rate of equal to or more than $8 \times 10^4$ for type A and at a dilution rate of equal to or more than $8 \times 10^3$ for type B, within 6 minutes of determination time (time until the density is stabilized).

B: Those for which comprehensive evaluation does not apply to either of A and C.

C: Those for which determination time is equal to or more than 8 minutes and equal to or less than 10 minutes.

D: Those for which determination time exceeds 10 minutes or those of which dilution rate capable of determination is equal to or less than $4 \times 10^4$ for type A and equal to or less than $4 \times 10^3$ for type B.

Experimental Examples 21 to 37

The preparation of the membrane carrier in Experimental Examples 21 to 37 was performed in the regions A, B1, and B2.

The experiment was performed in the same manner as in Experimental Example 1 except that the depth of the level difference, the diameter of the microstructure (convex portion), and the height of the microstructure (convex portion) were set as shown in Tables 3 and 4.

Subsequently, preparation of the detection zone, setting of the label, and evaluation of the detection were performed in the same manner as in Experimental Examples 1 to 17, except that the particles to be used were changed from colored latex particles to fluorescent latex particles (micromer-F fluorescent latex particles material polystyrene manufactured by Corefront Corporation), and 4 minutes after the start of the test, a magnification (limit magnification at which fluorescence can be determined), at which the presence or absence of a colored line could not be read by an immunochromatography reader (C11787 manufactured by Hamamatsu Photonics), was obtained. The results are shown in Tables 3 and 4.

Tables 3 and 4 also show the results of the comprehensive evaluation based on the following criteria for each experimental example.

A: Those of which limit magnification at which fluorescence can be determined 4 minutes after the start of the test is equal to or more than $1 \times 10^6$ for type A and equal to or more than $1 \times 10^5$ for type B.

B: Those for which comprehensive evaluation does not apply to either of A and C.

C: Those of which limit magnification at which fluorescence can be determined at 4 minutes after the start of the test is less than $7\times10^5$ for type A and less than $7\times10^4$ for type B.

Since the liquid sample test kit of the present embodiment can perform a highly sensitive test at a low cost, it is useful as a disposable POCT reagent.

According to the present embodiment, by using a flow path provided with an artificial fine convex portions having high design flexibility, it is possible to control the flow in the

TABLE 3

|  | Example 21 | Example 22 | Example 23 | Example 24 | Example 25 | Example 26 | Example 27 | Example 28 |
|---|---|---|---|---|---|---|---|---|
| Microstructure height of region A (μm) | 100 | 10 | 500 | 100 | 100 | 100 | 500 | 500 |
| Microstructure diameter of region A (μm) | 100 | 10 | 500 | 100 | 100 | 100 | 500 | 500 |
| Microstructure height of region B (μm) | 100 | 10 | 500 | 100 | 100 | 10 | 100 | 10 |
| Microstructure diameter of region B (pm) | 100 | 10 | 500 | 100 | 100 | 10 | 100 | 10 |
| Height of level difference (μm) | 100 | 10 | 500 | 50 | 200 | 100 | 500 | 500 |
| Limit magnification at which type A fluorescence determination is possible 4 minutes after start of test | $1 \times 10^6$ | $9 \times 10^5$ | $1 \times 10^6$ | $1 \times 10^6$ | $9 \times 10^5$ | $2 \times 10^6$ | $2 \times 10^6$ | $1 \times 10^6$ |
| Limit magnification at which type B fluorescence determination is possible 4 minutes after start of test | $1 \times 10^5$ | $9 \times 10^4$ | $1 \times 10^5$ | $1 \times 10^5$ | $9 \times 10^4$ | $2 \times 10^5$ | $2 \times 10^5$ | $1 \times 10^5$ |
| Comprehensive evaluation | A | B | A | A | B | A | A | A |
| Notes | Working Example | Working Example | Working Example | Working Example | Working Example | Working Example | Working Example | Working Example |

TABLE 4

|  | Example 29 | Example 30 | Example 31 | Example 32 | Example 33 | Example 34 | Example 35 | Example 36 | Example 37 |
|---|---|---|---|---|---|---|---|---|---|
| Microstructure height of region A (μm) | 100 | 100 | 100 | 100 | 500 | 500 | 100 | 500 | 500 |
| Microstructure diameter of region A (μm) | 100 | 100 | 100 | 100 | 500 | 500 | 100 | 500 | 500 |
| Microstructure height of region B1 (μm) | 100 | 100 | 100 | 10 | 100 | 10 | 10 | 100 | 10 |
| Microstructure diameter of region B1 (μm) | 100 | 100 | 100 | 10 | 100 | 10 | 10 | 100 | 10 |
| Microstructure height of region B2 (μm) | 100 | 100 | 100 | 10 | 100 | 10 | 100 | 500 | 500 |
| Microstructure diameter of region B2 (μm) | 100 | 100 | 100 | 10 | 100 | 10 | 100 | 500 | 500 |
| Height of level difference (μm) | 100 | 50 | 200 | 100 | 500 | 500 | 100 | 500 | 500 |
| Limit magnification at which type A fluorescence determination is possible 4 minutes after start of test | $2 \times 10^6$ | $2 \times 10^6$ | $1 \times 10^6$ | $2 \times 10^6$ | $1 \times 10^6$ | $1 \times 10^6$ | $2 \times 10^6$ | $2 \times 10^6$ | $1 \times 10^6$ |
| Limit magnification at which type B fluorescence determination is possible 4 minutes after start of test | $2 \times 10^5$ | $2 \times 10^5$ | $1 \times 10^5$ | $2 \times 10^5$ | $1 \times 10^5$ | $1 \times 10^5$ | $2 \times 10^5$ | $2 \times 10^5$ | $1 \times 10^5$ |
| Comprehensive evaluation | A | A | A | A | A | A | A | A | A |
| Notes | Working Example | Working Example | Working Example | Working Example | Working Example | Working Example | Working Example | Working Example | Working Example |

From the results of Tables 1 to 4, it was shown that the liquid sample test kit according to the present embodiment can promote stirring of the substance to be detected and the label by providing a level difference in the flow path, and can perform a highly sensitive test. It was shown that it was possible to suppress coloring of the background by preparing the detection zone on an inclined portion on a downstream side of the level difference, and thus the sensitivity was further improved. In addition, from the results of Tables 3 and 4, it was confirmed that highly sensitive test could be performed even in a case where the particles were fluorescent latex particles in the liquid sample test kit.

In a case where the level difference was not provided, high sensitivity was not obtained (Experimental Example 18). In a case where the height level of the bottom surface was lower on the downstream side than on the upstream side of the level difference, the liquid did not flow to the downstream side, and measurement was not possible (Experimental Example 19).

In a case where the amount of change in the height level of the bottom surface at the level difference exceeds twice the height of the microstructure on the upstream side of the level difference, the determination time was long (Experimental Example 20).

liquid sample test kit more easily compared to a technique of adjusting a pore diameter or thickness of a porous body having a non-uniform structure as in Patent Document 2. By providing a level difference in the flow path, stirring of a substance to be detected or a label is promoted, and it is possible to improve sensitivity in the detection zone compared to cases of Patent Documents 3 to 8 using a smooth artificial flow path.

In this application, priority is claimed on Japanese Patent Application No. 2017-236604, filed on Dec. 11, 2017, the content of which is incorporated herein by reference.

REFERENCE SIGNS LIST

2: flow path
3, 13: membrane carrier
3x, 13x: dropping zone
3y, 13y: detection zone
4: representative length at the bottom surface of the convex portion (diameter of the bottom surface of the convex portion)
5: distance between closest microstructures
6, 6a, 6b, 6c, 6d: height of convex portion
8, 8a, 8b, 8c, 8d: convex portion
7, 7a, 7b, 7c, 7d: microstructure 9: flat portion
10, 10, 10b, 10c, 10d: bottom surface of convex portion
18: liquid sample test kit
18a: housing
18b: first opening
18c: second opening
20: mold
20A: specific side
20B: opposite side of specific side 20A
20C: boundary between region B1 and region B2
A: first region
B: second region
B1: region
B2: region other than B1
d: flow direction of liquid sample (transporting direction)

The invention claimed is:

1. A membrane carrier for a liquid sample test kit that detects a substance to be detected in a liquid sample, the membrane carrier comprising:
   at least one integrally-molded flow path capable of transporting the liquid sample,
   wherein a microstructure that causes a capillary action for transporting the liquid sample is provided on a bottom surface of the at least one flow path,
   wherein the microstructure comprises a plurality of convex portions protruding from the bottom surface,
   wherein at least one level difference at which a height level of the bottom surface changes, is provided in the at least one flow path,
   wherein the at least one level difference is provided such that the height level of the bottom surface on a downstream side is higher than that on an upstream side in a transporting direction of the liquid sample and so as to cause stirring in a height direction in the liquid sample, and
   wherein a height of the plurality of convex portions on the downstream side is smaller than that on the upstream side with the at least one level difference as a boundary.

2. The membrane carrier for a liquid sample test kit according to claim 1,
   wherein the microstructure has any one of a cone, a pyramid, a truncated cone, a truncated pyramid, a cylinder, a polygonal prism, a hemisphere, and a semi-ellipsoid.

3. The membrane carrier for a liquid sample test kit according to claim 1,
   wherein an amount of change in the height level of the bottom surface at the at least one level difference is equal to or less than twice a height of the microstructure on the upstream side of the at east one level difference.

4. The membrane carrier for a liquid sample test kit according to claim 1,
   wherein an inclination in the at least one flow path is provided on the downstream side, such that the height level of the bottom surface approaches the height level on the upstream side of the at least one level difference.

5. The membrane carrier for a liquid sample test kit according to claim 1,
   wherein a height of the microstructure is equal to or more than 10 μm and equal to or less than 500 μm in the at least one flow path.

6. A liquid sample test kit that detects a substance to be detected in a liquid sample, the liquid sample test kit comprising:
   the membrane carrier for a liquid sample test kit according to claim 1,
   wherein the membrane carrier includes a detection zone that detects the substance to be detected in the liquid sample; and
   wherein in the detection zone, a change in color occurs at a time when the substance to be detected is detected.

7. A liquid sample test kit that detects a substance to be detected in a liquid sample,
   the liquid sample test kit comprising:
   a membrane carrier for the liquid sample test kit that detects a substance to be detected in a liquid sample,
   wherein the membrane carrier comprises at least one integrally-molded flow path capable of transporting the liquid sample,
   wherein a microstructure that causes a capillary action for transporting the liquid sample is provided on a bottom surface of the at least one flow path,
   wherein the microstructure comprises a plurality of convex portions protruding from the bottom surface,
   wherein at least one level difference at which a height level of the bottom surface changes, is provided in the at least one flow path,
   wherein the at least one level difference is provided such that the height level of the bottom surface on a downstream side is higher than that on an upstream side in a transporting direction of the liquid sample and so as to cause stirring in a height direction in the liquid sample,
   wherein the membrane carrier includes a detection zone that detects the substance to be detected in the liquid sample,
   wherein in the detection zone, a change in color occurs at a time when the substance to be detected is detected, and
   wherein the detection zone is provided on an inclined portion in the at least one flow path.

8. The liquid sample test kit according to claim 6,
   wherein a label having an antibody specifically reacting with the substance to be detected in the liquid sample or an antigen-binding fragment thereof is provided in at least a part of the liquid sample test kit so as to react with the substance to be detected, and
   wherein the change in color occurs due to the label that binds to the substance to be detected.

9. The liquid sample test kit according to claim 8,
   wherein the label is a particle in which the antibody or the antigen-binding fragment is bound to a colored latex particle or a fluorescent latex particle.

10. The liquid sample test kit according to claim 8,
    wherein a detection substance that detects the substance to be detected is immobilized in the detection zone, and the change in color occurs by the label being held in the detection zone by the detection substance and being colored.

11. A method of manufacturing the liquid sample test kit according to claim 6, the method comprising:
    immobilizing a detection substance in the detection zone, that causes the change in color by holding the substance to be detected in the detection zone.

12. A test method of a liquid sample using the liquid sample test kit according to claim 6, the test method comprising:
    mixing the liquid sample with a label specifically binding to the substance to be detected in the liquid sample to prepare a mixture liquid sample, and binding the substance to be detected and the label to each other;
    dropping the mixture liquid sample in a dropping zone provided on the membrane carrier;

transporting the mixture liquid sample from the dropping zone to the detection zone by the microstructure; and
detecting a change in color in the detection zone.

13. A membrane carrier for detecting a substance to be detected in a liquid sample, comprising:
at least one flow path,
wherein a microstructure is provided on a bottom surface of the at least one flow path,
wherein the microstructure comprises a plurality of convex portions protruding from the bottom surface,
wherein at least one level difference is provided in the at least one flow path, wherein the at least one level difference is provided such that a height level of the bottom surface on a downstream side is higher than that on an upstream side in a transporting direction of the liquid sample, so as to cause stirring in a height direction in the liquid sample, and
wherein a height of the plurality of convex portions on the downstream side is smaller than that on the upstream side with the at least one level difference as a boundary.

14. A membrane carrier for a liquid sample test kit that detects a substance to be detected in a liquid sample, the membrane carrier comprising:
at least one integrally-molded flow path capable of transporting the liquid sample,
wherein a microstructure that causes a capillary action for transporting the liquid sample is provided on a bottom surface of the at least one flow path,
wherein the microstructure comprises a plurality of convex portions protruding from the bottom surface,
wherein at least one level difference at which a height level of the bottom surface changes, is provided in the at least one flow path,
wherein the at least one level difference is provided such that the height level of the bottom surface on a downstream side is higher than that on an upstream side in a transporting direction of the liquid sample and so as to cause stirring in a height direction in the liquid sample,
wherein an inclination in the at least one flow path is provided on the downstream side, such that the height level of the bottom surface approaches the height level on the upstream side of the at least one level difference; and
wherein a detection zone is provided on an inclined portion in the at least one flow path.

15. The membrane carrier for a liquid sample test kit according to claim 1,
wherein the at least one level difference is provided on a downstream side of a part where a label is provided and an upstream side from a detection zone.

16. A membrane carrier for a liquid sample test kit that detects a substance to be detected in a liquid sample, the membrane carrier comprising:
at least one integrally-molded flow path capable of transporting the liquid sample,
wherein a microstructure that causes a capillary action for transporting the liquid sample is provided on a bottom surface of the at least one flow path,
wherein at least one level difference at which a height level of the bottom surface changes, is provided in the at least one flow path,
wherein the at least one level difference is provided such that the height level of the bottom surface on a downstream side is higher than that on an upstream side in a transporting direction of the liquid sample,
wherein an inclination is provided on the downstream side of the at least one level difference in the at least one flow path such that the height level of the bottom surface approaches the height level on the upstream side of the at least one level difference,
wherein the membrane carrier includes a detection zone that detects the substance to be detected in the liquid sample,
wherein in the detection zone, a change in color occurs at a time when the substance to be detected is detected, and
wherein the detection zone is provided on an inclined portion in the at least one flow path.

17. A membrane carrier for detecting a substance to be detected in a liquid sample, comprising:
at least one flow path,
wherein a microstructure is provided on a bottom surface of the at least one flow path,
wherein at least one level difference is provided in the at least one flow path, and
wherein the at least one level difference is provided such that a height level of the bottom surface on a downstream side is higher than that on an upstream side in a transporting direction of the liquid sample,
wherein an inclination in the at least one flow path is provided on the downstream side, such that the height level of the bottom surface approaches the height level on the upstream side of the at least one level difference, and
wherein the membrane carrier includes a detection zone that detects the substance to be detected in the liquid sample,
wherein in the detection zone, a change in color occurs at a time when the substance to be detected is detected, and
wherein the detection zone is provided on an inclined portion in the at least one flow path.

* * * * *